US005779998A

United States Patent [19]

Tom

[11] Patent Number: 5,779,998
[45] Date of Patent: *Jul. 14, 1998

[54] METHOD AND APPARATUS FOR CONCENTRATION AND RECOVERY OF HALOCARBONS FROM EFFLUENT GAS STREAMS

[75] Inventor: Glenn M. Tom, New Milford, Conn.

[73] Assignee: ATMI EcoSys Corporation, Danbury, Conn.

[*] Notice: The term of this patent shall not extend beyond the expiration date of Pat. No. 5,622,682.

[21] Appl. No.: 759,578

[22] Filed: Dec. 5, 1996

Related U.S. Application Data

[63] Continuation of Ser. No. 395,162, Feb. 27, 1995, Pat. No. 5,662,682, which is a continuation of Ser. No. 224,292, Apr. 6, 1994, abandoned.

[51] Int. Cl.⁶ .................................................. B01D 47/00
[52] U.S. Cl. .................. 423/210; 423/240 R; 423/240 S
[58] Field of Search ........................ 423/240 R, 240 S, 423/210, 219, 225, 230, 234, 235, 239.1, 241, 246, 247; 95/45, 47, 48, 49, 50, 51, 54, 96, 230, 232, 233, 234, 235, 236

[56] References Cited

U.S. PATENT DOCUMENTS

| | | | |
|---|---|---|---|
| 3,933,991 | 1/1976 | Dorn et al. | 423/535 |
| 4,070,164 | 1/1978 | Miwa et al. | 55/26 |
| 4,594,231 | 6/1986 | Nishino et al. | 423/240 S |
| 4,604,270 | 8/1986 | Tom | 423/210 |
| 4,645,516 | 2/1987 | Doshi | 55/16 |
| 4,964,137 | 10/1990 | Aramaki et al. | 372/59 |
| 5,091,358 | 2/1992 | Birbara et al. | 423/230 |
| 5,137,550 | 8/1992 | Hegarty et al. | 423/220 |
| 5,322,674 | 6/1994 | Mori | 423/240 |
| 5,622,682 | 4/1997 | Tom | 423/240 S |

FOREIGN PATENT DOCUMENTS

| | | | |
|---|---|---|---|
| 256692 | 5/1988 | Germany | 95/142 |
| 3-135410 | 6/1991 | Japan | |
| 4-118024 | 4/1992 | Japan | 423/240 |
| 2020566 | 11/1979 | United Kingdom | 95/142 |
| 88-01534 | 3/1988 | WIPO | 95/142 |

OTHER PUBLICATIONS

*Structural Chemistry of Inorganic Compounds*, Hückel, pp. 663–665 London, 1951 (no month).

*Chemical Principles*, 4th ed., Masterton and Slowinski, pp. 221–222, 1977 (no month).

*Inorganic Polymers*, Hunter, pp. 9–10, 1963 (no month).

"The Absorption Of Vapours By Activated And Heat–Treated Microporous Carbons–Part I . . . " R.H. Bradley, *Carbon*, 29(7), 893–897 (1991).

"Absorption Rate Coefficients For Gases And Vapors On Activated Carbons" Wood, G.O., Stampfer, J.F. *Carbon*, 31(1), 195–200 (1993).

SOLTRAP Product Literature, American Morikawa Industries corp., Feb. 3, 1994.

*Primary Examiner*—Michael Lewis
*Assistant Examiner*—Stuart L. Hendrickson
*Attorney, Agent, or Firm*—Steven J. Hultquist; Oliver A. M. Zitzmann

[57] ABSTRACT

A process for recovery of halocarbons from a gas mixture containing the halocarbon and acid gas components comprises the steps of contacting the gas mixture with a dry scrubber to remove the acid gas components from the gas mixture and yield a first effluent gas mixture containing the halocarbon. The first effluent gas mixture is contacted with an adsorbent which is selective for the halocarbon component of the first effluent gas mixture to adsorb the halocarbon component and yield a second effluent gas. The adsorbed halocarbon is recovered by desorbing same from the adsorbent. The process of contacting with adsorbent can be carried out in at least two adsorbent beds joined at inlet and outlet ends thereof to gas feed and gas discharge manifolds, respectively.

9 Claims, 4 Drawing Sheets

METHOD AND APPARATUS FOR CONCENTRATION AND RECOVERY OF HALOCARBONS FROM EFFLUENT GAS STREAMS

This is a continuation of U.S. application Ser. No. 08/395,162 now U.S. Pat. No. 5,622,682 filed Feb. 27, 1995, which in turn is a File Wrapper Continuation of U.S. application Ser. No. 08/224,292 filed Apr. 6, 1994 now abandoned.

BACKGROUND OF THE INVENTION

1. Field of the Invention

This invention relates to a method and apparatus for concentration and recovery of halocarbons from process effluent gas streams. The present invention further relates to a process of removing impurities from halocarbon-containing waste streams to enhance such concentration and recovery process.

2. Description of the Related Art

Fluorinated and chlorinated compounds are used in semiconductor etch, CVD, and cleaning processes. Examples of compounds which are widely used include perfluorocarbons, fluorinated hydrocarbons, and chlorofluorocarbons as well as sulfur hexafluoride, which will also be referred to herein as a "halocarbon." Examples are $C_2F_6$, $CF_4$, $CHF_3$, and $SF_6$. These compounds are suspected of causing global warming by a greenhouse effect. While long-term effects are unknown, current data suggest that compounds of this type are accumulating in increasing concentrations in the upper atmosphere, and that they can persist there for thousands of years. Manufacturers of many of these compounds, especially the perfluorocarbons (PFCs) are establishing policies that require customers to ensure that a high percentage of the PFCs are recycled or prevented from reaching the atmosphere.

Incineration as been shown to be an effective means of destroying halocarbons including PFCs. However, incineration requires considerable capital investment. In addition, because of the stability of PFCs, they must be heated to over 1200° C. before oxidation occurs. The reaction that takes place:

$$C_2F_6 + 2O_2 + 3H_2 \rightarrow 2CO_2 + 6HF$$

produces toxic and corrosive hydrogen fluoride, which must be neutralized. Typically, a wet scrubber would be used, adding to the overall cost and complexity, and generating large volumes of aqueous waste whose disposal may be inconvenient. Also, burning processes that involve hydrogen raise safety concerns. If the halocarbon is present in the effluent stream in a dilute concentration, incineration is especially cost-ineffective. In general, in the effluent streams from etch reactors, the halocarbon species is expected to be present in concentrations of only a few percent, e.g. 0.5–5%.

Pollution prevention and recycling is an approach potentially providing advantages to the environment as well as a simpler apparatus and methodology. Recovery and recycle are relatively simple for the liquid halocarbons, which can be trapped by refrigeration units. For the gaseous halocarbons, this approach may be too energy-intensive. However, because of their chemical inertness, the perfluorocarbons, $SF_6$, and the Freons that are used in the semiconductor industry are well-suited to recovery by adsorptive processes, such as pressure swing adsorption.

It is known that halocarbons may be adsorbed by various sorbent materials, including porous carbons, zeolites, silicas and aluminas. Wood and Stampfer (Carbon 31, pp. 195–200, 1993) studied adsorption for fifteen fluorocarbons on beds of activated carbon such as are used for removing gases and vapors from air. Their data may be used to predict the performance of a sorbent bed for any of these fluorocarbons after the bed has been characterized for one of the compounds. Packed beds of such activated carbons are used in applications ranging from air sampling tubes, respirator cartridges, to large industrial effluent filters, to adsorb halocarbons. Beds of porous adsorbent materials have been reported to be useful for the separation and recovery of volatile fluorocarbons.

Izumi et al. (Japanese Patent Application 03/135,410, 10 Jun., 1991) describes the adsorption of volatile substances including halocarbons on various high surface area adsorbents, such as gamma-alumina, activated carbon, high silica zeolite, silica superfine particles, or silica gel, at an adsorption pressure of 1–2 atmospheres, followed by desorption at a reduced pressure, preferably about ¹/₁₀ of the pressure at which the adsorption step took place. However, this process is better adapted to halocarbons which are liquids at room temperature, since the system provides liquified recovered halocarbon. Water is removed using an adsorbent such as K-A or NaA type zeolite, which adsorbs water but does not adsorb organic substances, from the concentrated halocarbon after it is desorbed from the sorbent bed. The presence of water vapor in the effluent gas stream from which the halocarbon is to be recovered causes problems, in particular, it limits the pressure at which the sorption step takes place to about one atmosphere. Such adsorption can be more efficient at higher pressures.

Recovery of fluorocarbons from semiconductor etch, CVD, and cleaning process effluents is, moreover, complicated by the presence of other toxic or corrosive components in the gaseous waste stream. Typically, the other waste gases can include corrosive species such as HF, or in for tungsten etch processes, $WOF_3$. Other species present can include $SiF_4$, $F_2$, or $COF_2$. Plasma processes may generate a large variety of by-product species because of chemical reactions such as rearrangement or scrambling that can occur in the high energy plasma. The table below presents a list of possible species in the exhaust of a reactor in which $C_2F_6$ is used in a plasma process for cleaning steps in silicon processing. Many of these materials are hazardous to both personnel and equipment because of their corrosivity and in some cases toxicity.

| AMI-5000 CVD CHAMBER CLEAN LIST OF POSSIBLE SPECIES IN EXHAUST STREAM | | | | | | |
|---|---|---|---|---|---|---|
| Name | Formula | MW | Vapor Pressure KPa | T °C. | Boiling T °C. | Critical T °C. |
| Carbonyl fluoride | $COF_2$ | 66.007 | 5,620 | 21.1 | −84.6 | 22.8 |
| Carbon dioxide | $CO_2$ | 44.011 | — | — | — | 31.1 |
| Carbon monoxide | CO | 28.010 | — | — | −191.5 | −140.2 |
| Carbon tetrafluoride | $CF_4$ | 88.005 | 1.33 | −169 | −128.0 | −45.6 |
| Decafluorobutane | $C_4F_{10}$ | 238.028 | 330 | 31.7 | −2.0 | 113.2 |
| 1,1-Difluoroethylene | $H_2C_2F_2$ | 64.035 | 3,571.5 | 21.1 | −85.7 | 29.7 |
| Dioxygen difluoride | $F_2O_2$ | 70.0 | 1.33 | −120 | — | — |
| Fluorine | $F_2$ | 37.997 | — | — | −188.1 | −128.8 |
| Hexafluorodisilane | $Si_2F_6$ | 170.162 | 0.0133 | −96 | — | — |
| Hexafluoroethane | $C_2F_6$ | 138.012 | 3,070 | 21.1 | −78.2 | 19.7 |
| Hexafluoropropylene | $C_3F_6$ | 150.023 | 687.4 | 21.1 | — | 94.0 |

-continued

AMI-5000 CVD CHAMBER CLEAN
LIST OF POSSIBLE SPECIES IN EXHAUST STREAM

| Name | Formula | MW | Vapor Pressure KPa | T °C. | Boiling T °C. | Critical T °C. |
|---|---|---|---|---|---|---|
| Hydrogen fluoride* | HF | 20.006 | 103 | 20 | 19.5 | 188.0 |
| Octafluorocyclobutane | $C_4F_8$ | 200.031 | 274 | 21.1 | −5.8 | 115.3 |
| Octafluoropropane | $C_3F_8$ | 188.021 | — | — | — | — |
| Oxygen difluoride | $F_2O$ | 53.996 | 0.0133 | −205 | −144.9 | −58.0 |
| Perfluoroisobutylene | $C_4F_8$ | 200.031 | — | — | — | — |
| Silicon tetrafluoride | $SiF_4$ | 104.08 | 0.0133 | −155 | — | −14.2 |
| Tetrafluoroethylene | $C_2F_4$ | 100.016 | 3,040 | 21.1 | −76.3 | 33.3 |

The presence of these other contaminants in process effluents can cause serious problems in adsorption-based recovery/recycle systems. The void space of the adsorbent can be filled with reaction products. This fouling of the adsorbent bed can destroy its ability to be regenerated, which seriously degrades the economics of recovery/recycle. In addition, the feed stream to for a recycling process needs to be as clean as possible to make recycle economically attractive. Allowing these corrosive contaminants to remain in the gaseous effluent stream can lead to corrosion of ductwork and valves, and eventually to system failure. And finally, environmental regulations prohibit venting significant quantities of HF or the other corrosive gases to the atmosphere.

In addition to these by-products generated from halocarbon starting materials in the wafer processing step, other hazardous components may be present in the effluent gas stream along with the halocarbon. Corrosive, reactive, flammable and/or poisonous gases may be used in processing steps along with the halocarbon or the effluent from which becomes mixed with the halocarbon-containing effluent gas stream. Examples include arsine (toxic) used in metalorganic chemical vapor deposition, boron trichloride (corrosive) used in etch or cleaning steps, silane (extremely flammable) used in silicide deposition, and tantalum pentaethoxide (solid-forming: rapidly hydrolyzes) used to deposit tantalum oxide.

Providing a relatively clean, dry, and inert incoming stream to a concentration and recovery unit will help to maximize its capacity as well as avoid hazards to personnel and equipment.

Removal of the contaminants from the process effluent stream can be accomplished by water-based scrubbers. Using wet scrubbing, the exhaust gas stream may be processed using aqueous solutions of relatively cheap reagents such as sodium hydroxide or potassium permanganate. However, wet scrubbing requires a large gas treating unit and the resulting large volumes of aqueous waste solutions may present problems as to environmentally acceptable disposal. In addition, the aqueous solutions used are very corrosive, and they thus can corrode fittings and connections and present risks to personnel and equipment in the event of an equipment failure. Water scrubbers require constant maintenance, and if the gaseous effluent contains highly flammable compounds such as silane (which is not soluble in water but reacts readily with oxygen), they present an explosion hazard. Moreover, for an adsorption-based concentration and recovery system to operate economically, the water vapor would then need to be removed from the scrubber effluent, or else the adsorption capacity of the sorbent bed would be largely consumed by water molecules which compete for the same adsorption sites. In addition, in most cases water would not desorb as readily as the halocarbon component from the adsorption bed. Therefore, water vapor contamination will, over time, seriously compromise the effectiveness of the concentration and recovery unit.

Dry scrubbing is preferred as a method for providing a relatively clean gas stream for recovery and recycle of halocarbons, because it does not contribute water vapor to the effluent stream. In addition, dry scrubbers operate passively and so do not require much energy or complicated equipment design.

With dry scrubbing, the flow characteristics and therefore the contact time of the gas with the scavenger may be adjusted by varying the porosity or particle size of the scavenger or selection of appropriate support material. In applications involving high flow rates, the scavenger may thereby be tailored for high kinetic efficiency; conversely under conditions of low flow, a highly loaded, high capacity support may be selected. To gain the advantages of both high efficiency and high capacity, scavenger beds may comprise more than one type of scavenger combination, in layered or mixed form.

A good effluent gas scrubber must not only remove hazardous gas components to low levels, preferably below their TLV/PEL limits, but must also possess several other attributes. It must operate safely, with no risk of explosion or spillage. It should have high capacity for the hazardous components, so that it need not require an extremely large volume for scrubbing or frequent change-outs. It must have high kinetic efficiency for scrubbing, so that high flow rate effluent gas streams may be scrubbed. Scrubbers of a simple, passive design are preferred, since they are likely to be more economical. Finally, the scrubber should convert the hazardous components of the effluent gas stream to stable, environmentally acceptable species that may be disposed of safely and economically.

In order to make recycling economically attractive, the concentration and recovery unit must be able to provide a concentrated stream of halocarbon for further purification or processing. Concentration of the recovered halocarbon gas or vapor may be accomplished by compression or liquefaction.

Accordingly, it is an object of the present invention to provide a method and apparatus for concentration and recovery of volatile halogenated compounds such as perfluorocarbons, fluorinated hydrocarbons, chlorofluorocarbons, and $SF_6$, all generically referred to herein as halocarbons. The method and apparatus are suitable for use with process effluents that may be contaminated with corrosive by-products, and is able to provide a clean, concentrated stream of recovered halogenated compound, suitable for recycle.

Other objects and advantages of the present invention will be more fully apparent from the ensuing disclosure and claims.

SUMMARY OF THE INVENTION

In one aspect, the present invention relates to a process for recovery of halocarbon from a gas mixture containing said halocarbon and acid gas component(s), comprising the steps of contacting the gas mixture with a scavenger composition scavengingly effective for the acid gas component(s) to remove said acid gas component(s) from the gas mixture and yield a first effluent gas mixture containing said halocarbon; contacting the first effluent gas mixture with an adsorbent which is adsorbingly selective for the halocarbon component of the first effluent gas mixture to adsorb said halocarbon component on the adsorbent and yield a second effluent gas; and recovering the adsorbed halocarbon by desorbing same from the adsorbent. The process of contacting with adsorbent can be carried out in at least two adsorbent beds via pressure swing adsorption processing of the first effluent gas mixture. The pressure swing adsorption processing may comprise provision of two, three, four or five adsorbent beds joined at inlet and outlet ends thereof to gas feed and gas discharge manifolds, respectively, wherein said first effluent gas mixture is introduced to one of said adsorbent beds at superatmospheric pressure to effect adsorption of halocarbon on the bed, and contemporaneously another adsorbent bed is depressurized following adsorption of halocarbon thereon, to desorb the adsorbed halocarbon and to discharge same from the bed at lower-than-first superatmospheric pressure, and wherein such steps are alternatively and repetitively carried out in the respective adsorbent beds.

In a further aspect of the invention, the process of contacting the gas mixture with a scavenger composition to remove acid gas components comprises contacting the gas mixture with a dry scrubber composition or with a liquid caustic solution. In another further aspect of the invention, the process for recovery of halocarbon may in addition comprise the use of a membrane selectively permeable to the non-halocarbon components of the gas stream.

Other aspects and features of the invention will be more fully apparent from the ensuing disclosure and claims.

DETAILED DESCRIPTION OF THE INVENTION, AND PREFERRED EMBODIMENTS THEREOF

The present invention employs a pressure swing adsorption (PSA) process to recover halocarbons from effluent gas streams in which they may be dilute, that is, present in concentrations of 0.1 to 5%. One objective of the invention is to achieve high recovery from a dilute stream, which is more difficult than the recovery of a gas at high purity from bulk streams. Application of thermodynamic principles to a potential PSA process shows that the theoretical maximum concentration increase is equal to the pressure ratio of the PSA times the inlet concentration for dilute components as follows:

$$Conc._{out} Max. = Concentration_{in} \times (Pressure_{ads}/Pressure_{desorp});$$

where $Conc._{out}$ Max. is the maximum outlet concentration from the PSA system for a dilute feed component; Pressure$_{ads}$ is the inlet pressure to the adsorption bed at pressure; and Pressure$_{desorb}$ is the lower desorption pressure during system operation.

This concentration increase limit however applies for a single pressure swing sequence and is obviously limited to a maximum value of 100%. The concentration increase can potentially be enhanced by a repeat of the cycle with the partially concentrated gas as the feed. Such a scheme may for example be used for high recovery of fluorocarbons (and $SF_6$) from gases containing oxygen and nitrogen. Sorption beds for a PSA process can be small (6" nominal diameter or less) and can be simple in design. Complexity is focused in the valving for operation and any extra compression and decompression steps. Automatic operation is preferred because of the rapid cycles utilized. Established PSA processes cycle from every few seconds up to perhaps every 10 minutes. The key is using an adsorbent material which is selective for the halogen-containing materials while it is non-selective or non-sorptive for the diluents (nitrogen and oxygen). High surface area adsorbents such as activated carbon, molecular sieves, aluminas, silica gel, and macroreticulate organic polymers such as Amberlite (Rohm & Haas) meet this requirement. Activated carbon is preferred.

Figure 1:
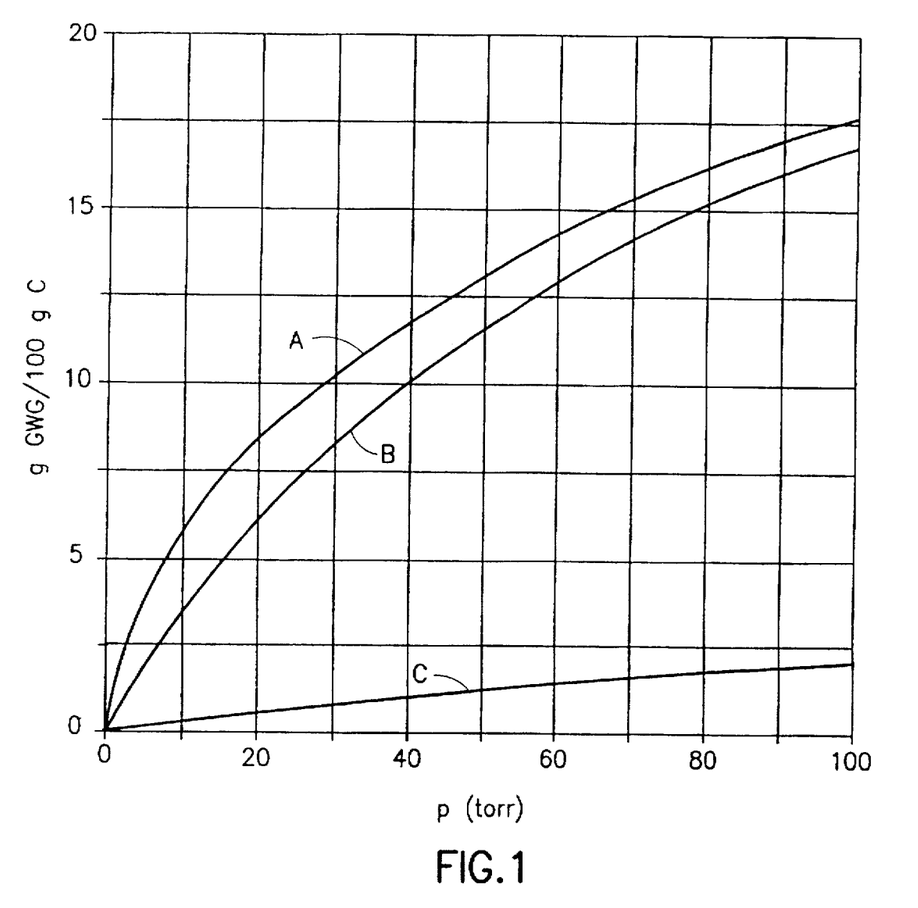
FIG. 1 shows adsorption isotherms for $C_2F_6$, $SF_6$, and $CF_4$ at room temperature on a bed of activated carbon of the type useful in the practice of the present invention.

Adsorption isotherms measured for activated carbon are shown in FIG. 1, which shows the amount (in grams) of halocarbon adsorbed per 100 grams of activated carbon versus halocarbon pressure (in torr). Curve A shows the results for $C_2F_6$, Curve B for $SF_6$, and Curve C for $CF_4$. These isotherms demonstrate that carbon is an acceptable sorbent bed. Apparatus for measurement of adsorption isotherms consisted of a small activated carbon bed (1" diameter stainless tube about 6" long) with a vacuum pump, pressure transmitter, and two temperature transmitters. Two mass flow controllers were connected to provide halocarbon and nitrogen at metered flows. The pressure transducer and temperature transmitters were connected to a computer for data collection and on-off control of the gas flows. Adsorption was measured near room temperature in the pressure range of 0-100 torr, which corresponds to a reasonable partial pressure for gases from dry pumped systems (the most dilute halocarbon stream anticipated from semiconductor processing effluents and therefore the most difficult case to handle in a concentration and recovery system), with a modest total system pressure of 100 psig. Gas chromatography was used to analyze the outlet flow.

Approximately one and a half weight percent $C_2F_6$ could be adsorbed onto Calgon BPL activated carbon at a pressure of 4.9 torr. Adsorptions were measured onto 17.1 g. of Calgon Carbon BPL. Runs were made at 80° C., 50° C. and 2° C. Temperature and pressure data were collected by computer. Mass flow data was controlled by an independent mass flow controller. The isotherms were made by adsorbing first at the higher temperature and then cooling the bed and the adsorption continued.

The total inventory of $C_2F_6$ in the bed was determined by multiplying the mass flow controller flow by the length of time gas flowed into the bed. Total volume of the bed was estimated at 220 ml which was subtracted from the amount of inventory in the system at pressure to calculate the amount of $C_2F_6$ adsorbed onto the carbon. It was found that the carbon quickly equilibrated in the small bed. Runs were generally made over a period of several hours.

$C_2F_6$ was removed from the activated carbon bed by vacuum. The removal rate was limited by the porous metal disk in the bottom of the bed ahead of the vacuum pump (rated at 3 cfm). After the run at 2° C., the constant temperature bath was removed and the bed evacuated. The temperature measurement (by RTD) was not calibrated below 0° C. and was below the range of the temperature transmitter, but the measurement clearly indicated substantial auto refrigeration in the carbon bed.

The heat of adsorption was calculated to be 61.4 cal/gm using the data at 50° C. and 80° C. and the Clausius-Clapeyron relationship. It was not possible to compare this to the latent heat of vaporization for $C_2F_6$ in this region because this temperature range is above the critical temperature of $C_2F_6$. Nonetheless, this latent heat is in the range for refrigerant type materials and similar to $C_2F_6$ below the critical temperature.

Figure 2:
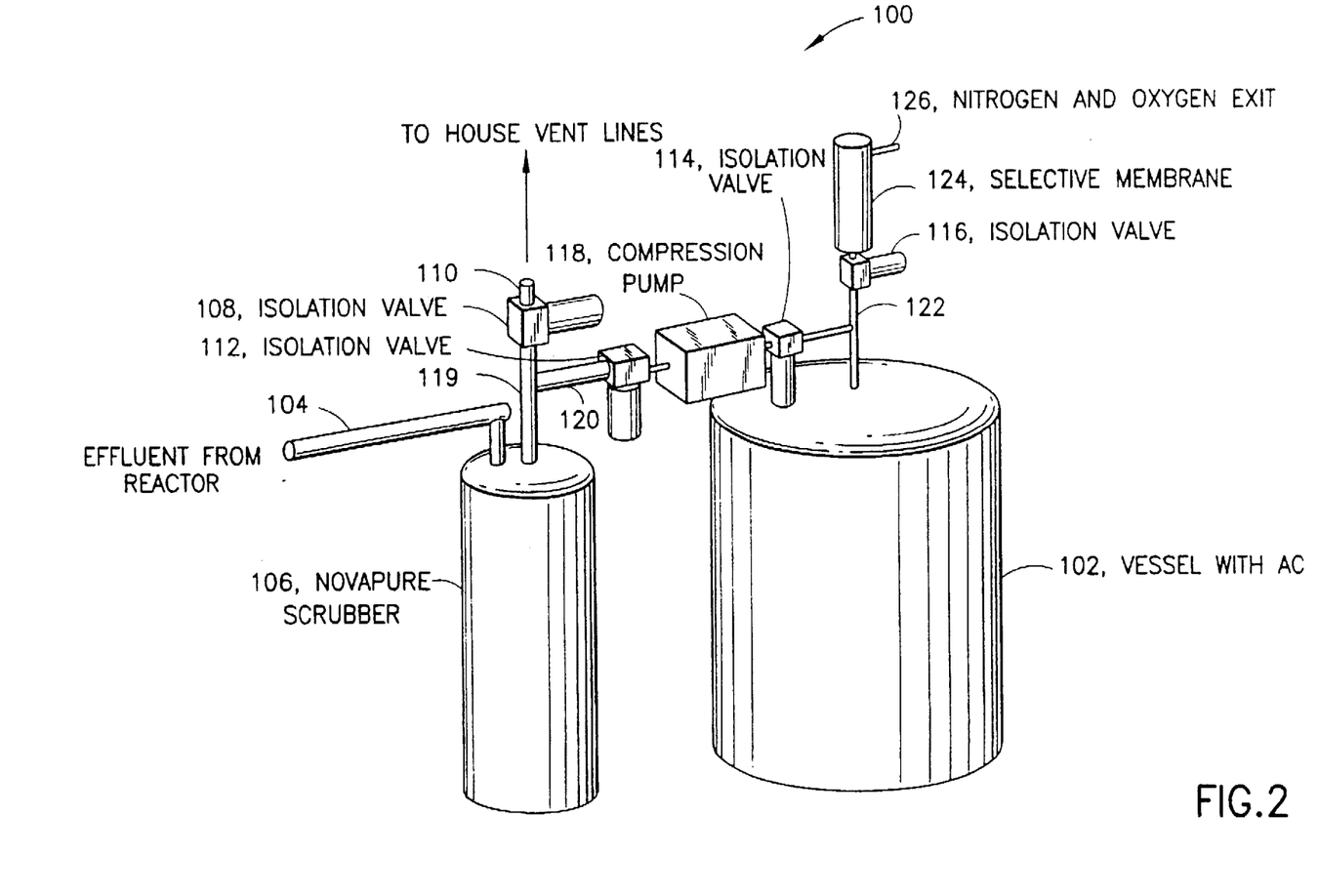
FIG. 2 shows a schematic of a simple system for recovery of halocarbons from effluent gas streams, employing one adsorbent bed, which is cycled between a high pressure adsorption step and a low pressure desorption step.

FIG. 2 shows a simple concentration and recovery process system 100 according to one embodiment of the present invention using one sorbent bed 102. The process effluent stream is flowed by conduit 104 from its source such as a semiconductor manufacturing plant (not shown) to scrubber vessel 166 for contacting with a scavenger in a scrubber bed of same in the vessel. In the scrubber vessel 106, the process effluent stream is treated in the scrubber bed by a scavenger to remove hazardous and solid-forming materials. On a signal (from the user or process monitoring means not shown in FIG. 2) that halocarbon is in the effluent stream, isolation valve 108 (joined to vent line 110) closes and isolation valves 112, 114, and 116 open. A compression pump 118 in conduit line 120 sweeps the remaining non-hazardous gas mixture through lines 119 and 120 into the vessel 102 which is filled with a suitable adsorbent for halocarbons such as activated carbon. When the pulse of halocarbon-containing effluent has passed, isolation valves 108 and 112 close. The halocarbons adsorb onto the carbon bed at a loading of up to 10% at 1 atmosphere. Nitrogen and possibly oxygen (which are not adsorbed by the adsorbent in vessel 102) flow through line 122 and isolation valve 116 therein to selective membrane device 124 equipped with diffused gas outlet conduit 126. The selective membrane device 124 comprises a selectively permeable membrane so that the non-adsorbed gases will diffuse out of the selective membrane and be discharged from the system in line 126. After the gas pressure in vessel 102 is reduced to a selected pressure level, isolation valve 116 will close. This adsorption process and concentration cycle can be repeated many times. The carbon bed can be used many times after desorption of the adsorbed halocarbon.

Selectively permeable membranes that are useful in this embodiment of the invention include cellulosics, polysulfones, and perfluorinated polymer membranes.

Figure 3:
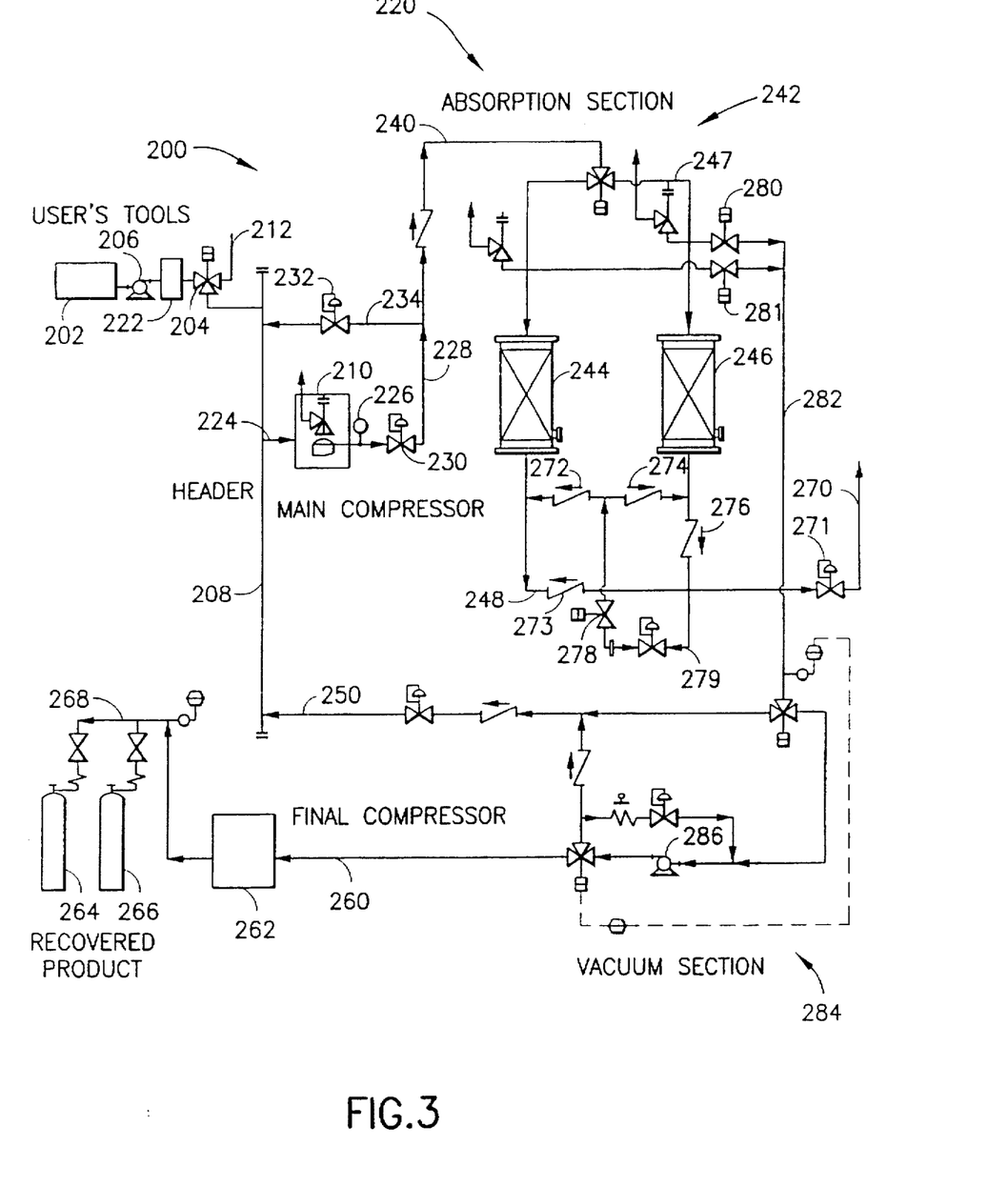
FIG. 3 shows a process flow schematic for the pre-scrubbing, concentration, and recovery steps that comprise one embodiment of the method of the present invention, employing two canisters of adsorbent which are pressure-cycled alternately to provide continuous service.

FIG. 3 shows a block flow diagram for a process system 200 according to another embodiment of the invention, for processing halocarbon-containing gas mixtures from a semiconductor wafer fabrication facility including wafer fabrication tool 202. A brief description of each block follows.

Collection of the halocarbon gases is accomplished at the wafer fabrication tool 202 ahead of any scrubbers. A tie-in is made with a three-way valve 204 which routes gases after the tool's vacuum pump exhaust, from vacuum pump 206 through scrubber 222 to other existing treatment equipment (not shown) or simple discharge via discharge line 212 or to the recovery system 220. Each separate source of halocarbon from a multisource (multitool) process system suitably has a tie-in similar to that shown with a three-way valve for control of the collected gas flow. Such a system allows operation when there are no halocarbons at the fab tool, as the fab system conventionally operates, by routing the gas discharge through the discharge line 212. During tool operation with a halocarbon flow, the three-way valve 204 routes the stream (after the fab tool vacuum pump 206) from the scrubber vessel 222 into a collection header 208.

The collection header 208 is maintained at slight negative pressure and has no adverse impact upon the wafer fabrication tool 202. From collection header 208, the gas mixture is passed in feed line 224 to compressor 210.

Compression of the collected gases to about 100–150 psig (about 7.8–10 atmospheres) is accomplished with the compressor 210. In one embodiment of the invention, this compressor may be a liquid ring compressor which operates with a recirculated dilute caustic liquid seal. The liquid ring compressor can be operated with its suction controlled at a slight negative pressure as mentioned above. A description of liquid ring compression can be found in Perry's Chemical Engineers' Handbook. Other compressor types which may also suitably be employed include piston compressors, gear compressors, and rotary vane compressors.

Collection header pressure is suitably monitored by a pressure gauge 226 in pump discharge line 228 which is immediately upstream of back-pressure regulator 230 in discharge line 228. Flow control valve 232 in header recycle line 234 releases gas as required to control the collection header pressure and maintain a selected load level on the compressor 210.

Any acid gases (for example, HF, $H_2SiF_6$, $BCl_3$, HCl, $Cl_2$, $SiF_4$) remaining in the collected streams are flowed to collection header 208, absorbed and neutralized by the dilute caustic used as seal liquid in the compressor 210.

When compressor 210 comprises a liquid ring pump, dehydration of the caustic neutralized gas is required because water generally interferes with carbon adsorption and selectivity. System operation with dry scrubbers and dry compression equipment may be employed and the actual compression sequence selected on technical and economic grounds. Dehydration of the compressed gas can be accomplished by a heat-less dryer (not shown) which is designed for this process. A two bed heatless dryer can be used which is identical to dryers used for compressed air except that the dryer exhaust is suitably recycled back to the compressor suction of compressor 210 so as to avoid any unnecessary loss of halocarbon gas. For a compressor discharge pressure of 100 psig, the flow of gas for reactivation of the dryer beds will be about 15–20% of the compressor flow.

Halocarbon concentration is accomplished by a pressure swing adsorption process (PSA) carried out in the PSA system 242 comprising adsorbent beds 244 and 246 and cooperatively coupled with each other between a first PSA manifold 247 and a second PSA manifold 248 in a known and conventional manner. Multiple bed PSA systems utilizing two or more beds manifolded together for intermittent or continuous adsorption operation of widely varying types may be used in the broad practice of the present invention. A three-bed cascade adsorption system is described, for example, in Bulkeley, *Chem. Met. Eng.*, 45, 300 (1938), and U.S. Pat. Nos. 4,070,164 ("Adsorption-Desorption Pressure Swing Gas Separation") and 4,645,516 ("Enhanced Gas Separation Process") describe other potentially useful PSA systems. The disclosures of these references hereby are incorporated herein by reference.

The desired product (concentrated halocarbon stream) of the PSA processing is the material retained on the adsorbent. A simple description of the sequence follows.

At system pressure (70–200 psig, preferably 100–120 psig), the halocarbon-containing gas is passed through one of the adsorbent beds 244 and 246, where the halocarbon is adsorbed onto the bed and the gas vented through line 248 and back-pressure regulator 271 and exit line 270. If adsorbent bed 244 is the currently active adsorbing bed, then bed 246 is being regenerated, and actuated valve 280 is open and gas flows in line 282 to the vacuum section 284. Check valves 272, 273, 274 and 276 direct flow and prevent backflow into the canister that is being regenerated. When adsorbent bed 244 is serving as the active adsorber, valve 278 in conduit line 279 is closed, thereby preventing gas flow to check valve 274 and therefore preventing back-flow to adsorbent bed 246. Check valve 276 prevents back-filling of adsorbent bed 246.

The partly depressurized bed is additionally vented countercurrently back into the compressor suction of compressor 210 via lines 240 and 234, or alternatively, in lines 250, 208 and 224 (depending on which bed is actively adsorbing and which bed is regenerating).

Concentration of the halocarbon occurs during the desorption step when the partial pressure is similar to the adsorption partial pressure, but the system total pressure is substantially lower.

After the bed that is being regenerated, adsorber bed 246, is suitably clean, valve 278 is opened and the vent gas from the active adsorber 244 is used to back-fill in a counter current fashion the just-regenerated adsorber bed 246.

After the pressure in 246 is suitably high, the valves are switched to make it the active adsorbing tank. The tank 244 that was the active adsorbing tank is now regenerated. One bed is always on stream for adsorption.

The vacuum pump section 284 is set up to protect the vacuum pump 286 from high pressures. Until the pressure in line 282 reaches a suitably low level, the gas is routed through line 250 back to the main header line 208. The gas stream contains halocarbons that may be recovered on subsequent passes through the adsorber bed(s). Vacuum section 284 is further equipped to increase the concentration of halocarbon by venting more of the dilute halocarbon mixture back into the header line for recovery. When the concentration of halocarbon becomes suitably high, the gases are routed through line 260 to be compressed by compressor pump 262.

Compression of the recovered halocarbon is relatively inexpensive and is carried out by flowing the halocarbon in product line 260 to a three stage compressor system 262. One or more cylinders 264, 266 may be connected to a filling header 268 which operates under automatic control to package the recovered halocarbon for recycle, disposition or other use.

Depending upon the initial concentration of halocarbon and the pressure ratios employed as well as the process design, it may be desirable to repeat the above sequence with the concentrated halocarbon product from the above described sequence. Experimental data as well as the purity and concentration requirements for recycling may readily be used to determine if a second stage of compression and PSA is required.

In the practice of the present invention, the adsorbent for adsorbing the halocarbon is selected on the basis of is capacity for halocarbon as well as its Suitable materials include high surface area adsorbents such as activated carbon, molecular sieves, aluminas, silica gel, and macroreticulate organic polymers such as Amberlite. Activated carbon is preferred. Carbon is an excellent adsorbent for halocarbons; its high polarizability suits it well for adsorption of non-polar molecules such as $C_2F_6$, $CF_4$, and related species.

If an activated carbon adsorbent bed(s) is characterized as to its capacity for one of the halocarbon gases, its adsorptive performance may be predicted for many other halocarbon species using data published by Wood and Stampfer (*Carbon* 31, 195–200, 1993; *Carbon* 30, 593, 1992) and by Nelson et al. (*Am. Ind. Hyg. Assoc. J.* 33, 797 (1972); *Am. Ind. Hyg. Assoc. J.* 52, 235 (1991)).

Etch or cleaning steps in semiconductor wafer fabrication generate, in addition to unreacted halocarbons, harmful acidic and solid-forming contaminants in the process effluent gas stream, as well as possibly other toxic or flammable species that are used in wafer fabrication steps. The process of concentration and recovery of halocarbons from these effluent gas streams by one embodiment of the present invention preferably incorporates dry scrubbing to remove these acidic and solid-forming contaminants and/or other hazardous gas species such as flammables or toxics.

Suitable scavengers for use in the dry scrubbing step include many metal oxide- or hydroxide-based solid chemisorbent materials that are well-known in the art. Examples of these scavengers include materials whose active scavenging species are goethite (FeOOH), copper oxide, copper oxide/zinc oxide mixtures, copper sulfate, calcium oxide, lithium hydroxide, and related compounds. Useful scavengers include metallic macromer scavengers described in U.S. patent application Ser. No. 08/179,441 ("Metallo-Oxomeric Scrubber Compositions, and Method of Gas Purification Using the Same") and U.S. Pat. Nos. 5,151,395, 4,743,435, 4,996,030, 5,024,823 and 4,535,072, the disclosures of U.S. Pat. Nos. 5,151,395; 4,743,435; 4,996,030; 5,024,823 and 4,535,072 are hereby incorporated herein by reference.

The metallic macromer scavengers provide reactive scavenger compositions which, when used as scrubber media in heterogeneous reactors employed for hazardous gas abatement, provide improved volumetric efficiency over currently employed scavengers, especially for scrubbing acidic gas effluents. The scavenger compositions are composed (to the extent practical) only of moieties which react with the species of interest present in the stream. To form effective scrubber media, the scavenger compositions are rendered into forms that have minimal void space, thus placing the maximum amount of chemically reactive species practical within the reactor volume. Merely filling the available reactor space with reactive materials does not necessarily lead to utilization of the bulk of the scavenger, but the metallic macromer scavenger compositions, when used to scrub acidic effluent gases, ablate to continually provide fresh flow pathways and access to the reactive species. Therefore their capacity to react with the hazardous gas components is maximized.

In the metallic macromer scavengers, maximum utilization is accomplished by preparation of a scrubber mass composed of polymeric strands that consist of transition metal centers bridged by organic and/or inorganic moieties. Illustrative formulas are:

-continued

The metal center M should be able to coordinate about it m number of charged moieties, shown as the type a or b moieties above, based upon its charge. Thus, the number of each type of moiety interacting with a particular metal center in this fashion may be any number from 0–m. If m=2, for example iron(II), the metal could be coordinated to 0, 1, or 2 type a moieties (for example, carbonates) and correspondingly 2, 1 or 0 type b moieties (for example, dicarboxylates). Furthermore, the metal centers may be linked by repeating units of a random number of type a and b moieties bridging between metal centers. In the representative formulas shown above, these are shown as type X and Y repeat units. The number of times a repeat unit appears in a particular chain of bridged metal centers may be any number from 0 to the maximum number of subunits appearing in a particular chain. The type b bridging moieties may contain from 2 up to z anionic ends which may participate in the formation of chains of z−1 dimensions through interaction with up to z metal centers.

Polymeric materials of the metallic macromer scavengers, in which the metals are bridging as shown in the representative formulas above, are preferred over polymers in which the metals are merely coordinated to active sites in an organic polymer, because of this the metallic macromer polymers can scrub acid gases ablatively. Additionally, it will be appreciated that metal centers after having coordinated sufficient charged species to satisfy their valence requirements may coordinate p number of additional moieties in the manner represented in the lower formula above. The illustration depicts coordinative bonding to a metal center of a second polymer chain by electron lone pairs from p-bonded oxygen moieties in the first chain. It can be appreciated that any species with polarizable electron pairs can participate in this type of interchain coordination. This applies equally well to the oxygen lone pairs of carbonate moieties (type a fragments). The number of additionally coordinated moieties (value of p) depends upon the nature of the particular metal center employed. Thus, the R group of type b bridging moieties may contain structures which interact chemically according to the general principles expounded herein for simple difunctional bridging species, yet lead to more complex polymeric structures than illustrated here.

Polymers made using these principles are unstable in the presence of the hazardous species which the mass is intended to scrub, and when such species are present the mass depolymerizes with the formation of stable metal adducts. Additionally, some of the bridging species are selected so that, upon reaction with certain hazardous components of the gas stream, volatile products are formed, creating openings in the scrubber mass and thereby providing access pathways for the hazardous moieties to contact fresh material within the mass.

Metals are selected based on the following criteria. The metal itself should not be toxic, or the ultimate disposal of the spent scrubber medium will become difficult. Metals that have more than one accessible oxidation state are preferred. The cost of the metal must be reasonably low, to enable production of economical scrubber media. Transition metals of groups IB, IIB, IVB, VIB, VIIB, and VIIIB are advantageous, with group VIIIB and IB metals being preferred and iron in the dipositive oxidation state most preferred.

The "oxomeric" bridging species are oxygen-containing groups which are covalently bondable to the metal coordination atoms in the macromeric complex of the metallic macromer scavengers, and comprise at least one repeating unit of —O—C(O)—O—, —O—C(O)—, —O—S(O)—O—, —O—Si(O)$_2$—O—, optionally interconnected between successive repeating units of such formulae by a divalent organo group, such as alkylene. At least one oxo (—O—) group coordinates with the metal. These oxomeric bridging groups must also be selected on the basis of functional groups, absence of significant toxicity, and low cost. Bridging species are selected from the group of carbonates, di- or polyfunctional carboxylates, di- or polyfunctional oxy- and hydroxycarboxylates, di- or polyfunctional phosphorous, sulfurous, nitrogenous, and silicious oxides, borates, chlorates, aluminates, sulfamates, di- or polyfunctional aminates, and discrete organics containing di- or polyfunctional analogs of any of this class of materials. Carbonate, carboxylate, sulfite, and silicate are the preferred bridging species. Of the carboxylates, malonate, malate, succinate, adipate, citrate, and other hydroxy carboxylic acids are especially useful because they can be formulated into very effective scavengers and have low cost and low toxicity.

In a preferred embodiment of the metallic macromer scavengers, the bridging species are combined in such a way as to yield a mass having carbonate, carboxylate, and third member bridging moieties coordinated to the metal center so that the ratio:

metal/carbonate/carboxylate/third member bridging moieties falls within the range of 1/0–2/0–2/0–2.

Preferred embodiments have mole ratios:

iron/carbonate/carboxylate/sulfite of approximately 1/0.5–0.98/0.02–0.5/0 and 1/0.5–0.98/0.02–0.5/0.02–0.6.

With the inclusion of sulfite, the latter formulation is especially useful for scrubbing halogens such as chlorine. Racemic malate is especially preferred as the carboxylate species, since it is cheap, of low toxicity, and may be formulated into an effective scavenger.

Reactive scavengers can be designed such that the products arising from the reaction of one hazardous species may be used to react with and trap a second, different hazardous species, increasing the utility of a given reactive scavenger mass for mixed gaseous effluent streams. Mixed effluents streams are generated by many etch processes which generate gaseous acid waste as well as chlorine or other halogen. Scrubber media used to scrub hydrogen chloride to total exhaustion of scrubbing capacity have further capacity to scrub chlorine, as described in more detail in Example 7 below. However, it can readily be appreciated that these advantages are readily extendible to any gaseous waste stream containing moieties capable of entering into a chemical reaction.

The metallic macromer scavenger compositions must have a physical morphology that is suitable for scrubbing a gas stream without compressing, fracturing to form dust, or in any other way clogging conduits or blocking the flow of gas. The scavengers are suitably pelletized, extruded, otherwise shaped or employed in monolithic form. To this end the metallic macromer scavengers may employ binder materials whose flnction is to provide physical stability and improved handling properties. The metallic macromer scavengers preferably employ a 1–25 weight percent of sodium silicate to serve as a binder. The addition of sodium silicate during preparation of the scavengers causes the reaction product to precipitate. allowing easy separation of the reactive mass and processing solvent. The silicate also forms an inert mass which interpenetrates the reactive mass. providing a stabilizing structure to the reactive mass as it is consumed during its use as a scrubber.

Other hydrated materials capable of gelation and subsequent formation of a metal oxide glassy matrix would serve the binder function equally well. such as hydrated titanium oxides, zirconium oxides. phosphates. or zinc oxides. In order to scrub some of the noxious gases that can be present in semiconductor etch or CVD process effluents. such as phosgene ($COCl_2$) or carbonyl fluoride ($COF_2$). quite basic sites may be needed. If so. more basic oxides such as zinc oxide or calcium oxide will be useful binder materials. Inert additives such as molybdenum disulfide. which provides a rubbery texture. can be employed as binders.

The metallic macromer scavenger compositions may be synthesized by a number of different procedures. Two major processes and variants upon these processes are disclosed. These may be broadly classified as "building up" strands of reactive material by stepwise addition of subunits of the reactive mass. or simultaneous precipitation of randomly organized moieties by reaction of a precursor transition metal carbonate with an organic acid.

Reactive scavenger masses of the type in the metallic macromer scavengers may be synthesized containing only carbonate and iron with a binder material or containing any one of a wide variety of polyfunctional carboxylates and other bridging moieties useful in scrubbing hazardous materials other than acid gases. such as sulfite for the purpose of scrubbing chlorine or other halogens.

Scavengers containing only carbonate and metal with a binder material can be prepared by. for example. allowing aqueous or alcoholic solutions of iron(II) chloride and sodium carbonate to react under nitrogen. A binder solution may optionally be added to the carbonate solution before addition of the iron chloride. After the reaction mixture has been stirred and heated. the product is dried under an inert atmosphere. This type of preparation is exemplified by the iron carbonate scavengers prepared in Example 1. Samples 1 and 2 below.

One synthetic procedure allows for the random, simultaneous reaction of a number of moieties placed into solution together. In this method (exemplified below in Example 1 for Samples 3. 4. 6. 8. and 9). a dicarboxylic acid and a transition metal salt are dissolved in water to a specific molar ratio. $NaHCO_3$ and/or $Na_2CO_3$ solution is added to this mixture. This addition deprotonates the dicarboxylic acid to yield a form capable of reaction with the transition metal chloride. while at the same time the alkali carbonate is also capable of reacting with the transition metal chloride. The result is the formation and precipitation of randomly organized "chains" of material containing the transition metal bridged to other transition metal centers through either the dicarboxylic acid or carbonate moiety.

A variation on this strategy (exemplified below in Example 1 for Samples 5 and 7) is to form the soluble transition metal complex $LiCO_3MCO_3Li$ (where M is a suitable transition metal) as a precursor species. This species is then allowed to react with limited quantities of dicarboxylic acid. which removes bicarbonate moieties from the transition metal to form the carboxylate. Control of the stoichiometry and concentration of the species involved leads to the formation of structures of random length wherein transition metal centers are bridged by carbonates and carboxylate moieties.

An alternative method (exemplified below in Example 1 for Sample 10) is to precipitate the transition metal carbonate. take the precipitate up into an aqueous slurry. and infuse carboxylic acid into the slurry. The carboxylic acid reacts randomly with transition metal carbonate bridging moieties. resulting in the random insertion of carboxylate moieties into the structure.

The preferred embodiment of the metallic macromer scavengers yields material containing a transition metal selected from the group of first second and third row transition metals of groups IB. IIB. IVB. VIB. VIIB. and VIIIB. with group VIIIB and IB metals being preferred. and iron in the dipositive oxidation state the most preferred. and an oxomeric bridging species selected from the group of carbonates. di- or polyfunctional carboxylates. di- or polyfunctional oxy and hydroxy carboxylates. di- or polyfunctional phosphorous. sulfurous. nitrogenous. and silicious oxides. chlorates. borates. aluminates. sulfamates. di- or polyfunctional aminates. and discrete organics containing di- or polyfunctional analogs of any of this class of materials. with carbonate. carboxylate and sulfite preferred as bridging species. Combinations of carbonate and carboxylate selected from the group malate. malonate, succinate. adipate. and citrate are most preferred for acid gas scrubbing. with the addition of sulfite for chlorine scrubbing capability. The scavenger compositions as synthesized contain carbonate. carboxylate. and third member bridging moieties coordinated to the metal center. They are prepared such that the mole ratio of reactants Fe salt/carbonate/($CO_2$)$_2$R/third member bridging moieties lies in a range of 1:2:0:0. 1:0:2:0. and 1:0:0:2, with the most preferred embodiments being combinations of reactants such that the ratio:

metal/carbonate/carboxylate/third member bridging moieties falls within the range of 1/0–2/0–2/0–2.

Preferred embodiments have mole ratios of reactants:

iron/carbonate/carboxylate/sulfite of approximately 1/0.25–0.75/0.25–0.75/0 and 1/0.2–0.5/0.2–0.5/0.2–0.6.

To convert the reactive scavenger mass into a physical form usable for scrubbing a gas stream in a simple canister. it is necessary to render the reaction product into a pelletized. shaped or monolithic form. To this end. a 1–25 weight percent sodium silicate solution may be added during synthesis to serve as a binder. When mixed with the reactive mass as it exists in the reaction vessel following its preparation. sodium silicate renders the moieties comprising the reactive scavenger mass insoluble in the process solution. thus permitting easy separation of the reactive scavenger mass and processing solvent by filtration. decantation. centrifugation. or other appropriate means.

In a preferred embodiment. the metallic macromer scavenger employs iron in the +2 oxidation state. Such Fe(II)-based scavengers can scrub halogens by a redox reaction, which Fe(III)-based scavengers cannot. In addition. by contrast with iron(III). iron(II) forms a stable carbonate. This carbonate is acid-unstable and scrubs acids by a reaction that forms carbon dioxide. Thus scavengers containing iron(II) carbonate moieties can scrub acidic gases ablatively. which allows fresh scavenger surface to be continually exposed. An ablative scrubbing mechanism leads to higher capacities and less likelihood of clogging.

For practical use, scavengers that are stable to oxidation in air at room temperature are preferred. Stabilizing the iron(II) oxidation state requires the presence of stabilizing species such as the carboxylate and silicate moieties. In practice, the air stability of the iron(II)-based scrubbers of the metallic macromer scavengers depends on the proportions of iron, silicate binder, and hydroxycarboxylate moiety. The iron(II) carbonate material as prepared by the method taught herein is not air-stable, but becomes so as the proportions of carboxylate and silicate are increased. However, if the carbonate is totally replaced by silicate, the scavenger, while completely air-stable, has no scrubbing capacity. Thus the silicate must be present in a proportion sufficient to impart the desired physical properties but not so high as to remove scrubbing capacity. A particularly preferred embodiment uses carbonate, carboxylate, and iron in approximately equimolar quantities in the reactant mixture with 0–0.5 mole fraction silicate.

The silicate also forms an inert mass which interpenetrates the reactive scavenger mass, physically stabilizing the reactive scavenger mass as it is consumed during its use as a scrubber. Other hydrated materials capable of gelation and subsequent formation of a metal oxide glassy matrix would serve this function equally well. In a preferred embodiment of the metallic macromer scavengers, the reactive mass is combined with binder, separated from the processing solvent, and formed into "noodles" by extrusion through a die plate. Before it is dried, the scrubber medium is reasonably plastic and would just as easily lend itself to being formed into a number of shapes for use as monolithic elements.

The combined reactive mass and binder may be dried in air at ambient conditions or in a vacuum chamber at moderate temperatures. The material must be dried to the point where sufficient water of hydration has been removed to allow three dimensional polymerization to occur. It is not desirable to remove all of the water. Acid halides such as boron trichloride must be hydrolyzed to be scrubbed, and if the scavenger is completely dry, it will not be able to scrub such noxious species. The amount of water retained in the scavenger composition should be in the range of 5–50 weight percent, with 10–20% preferred, and 11–15% most preferred. A filter press can be used initially to squeeze out most of the water to be removed, with the remainder to be removed by drying under air or nitrogen at room temperature or at temperatures up to 100° C. at most, but preferably under 50° C.

The scavenger compositions as prepared are very insoluble in water, alcohol or other common solvents. For the preferred iron-based scavengers, the amount of iron that could be extracted out of the scavenger material was assayed colorimetrically. Essentially no measurable iron was detected in the aqueous supernatant after mixing the scavenger materials with water. This lack of water-solubility is in contrast to the behavior of the starting materials, most of which are highly water-soluble compounds such as hydroxycarboxylic acids or iron(II) salts. In addition, during scavenger preparation there is a dramatic increase in viscosity of the scavenger suspensions during preparation. The materials typically become very gelatinous or thick during the reaction.

The metallic macromer scavengers are stable upon storage at room temperature. Exposure to air or moisture does not compromise the effectiveness of the scrubbing process.

Figure 4:
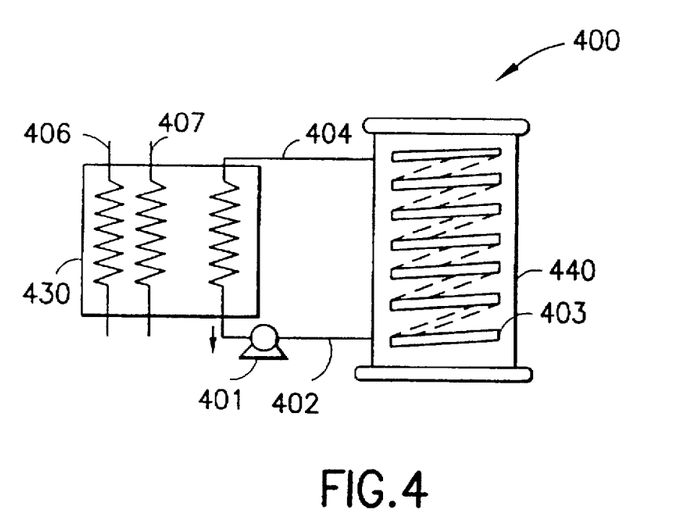
FIG. 4 shows a heat exchange system that can be used to accomplish temperature control during the PSA process.

The pressure swing adsorption process becomes more efficient if temperature is controlled during the adsorption and desorption cycles. FIG. 4 shows one example of a heat exchange system that can be used to accomplish temperature control during the PSA process. Temperature-controlled adsorber system 400 is equipped with a pump 401 for circulating a cooling fluid from a heat exchange unit 430 through conduit line 402 into the adsorber-containing canister 440. The fluid circulates through coils 403, emerging from the canister via conduit line 404 for return to the heat exchange unit 430. Elements 406 and 407 provide heating and cooling respectively. Heat is provided during the desorption step and cooling is provided during compression/adsorption.

The features and advantages of the metallic macromer scavengers are more fully illustrated by the following non-limited example, wherein all parts and percentages are by weight, unless otherwise expressly stated, and solution concentrations are molal (m) unless otherwise denoted.

EXAMPLE

Preparation of Scrubber Samples

Sample 1

Aqueous 5.116 molal $FeCl_2$ and 0.304 molal $Na_2CO_3$ solutions were prepared. Using these solutions, 0.50 moles $FeCl_2$ was placed into a vessel under a nitrogen purge. 0.50 moles $Na_2CO_3$ was added drop-wise to the $FeCl_2$ solution. The resulting solution was held unstirred under an inert atmosphere for 12 hours at room temperature. A clear supernatant layer formed and was decanted. A brown precipitate was separated from the remaining aqueous supernatant by gravity filtration. The resulting mud-like residue was dried under a nitrogen stream. The dry material was light tan to brown and rocky in appearance; it was broken into irregular chunks or granules larger than 8 mesh, with most approximately 12×20 mesh.

Sample 2

A "Water Glass" solution having a nominal stoichiometry of $Na_2O(SiO_2)_2$ was made by dissolving 0.941 moles of silica gel in 160 ml of $H_2O$ with the aid of 0.472 moles NaOH. The final density of this solution was 1.92 g/ml. 1.744 molal aqueous $Na_2CO_3$ and 1.280 molal methanolic $FeCl_2$ solutions were prepared. Using these solutions, 0.218 moles of $Na_2CO_3$ was placed into a vessel, blanketed with nitrogen, and heated to 35° C. Into the whole of the sodium carbonate solution was added in one aliquot 5 ml of the "water glass" solution with stirring. To the resultant solution was added in one aliquot an amount of the iron chloride solution containing 0.081 moles of $FeCl_2$. Throughout additions an inert blanket of nitrogen and a temperature of 35° C. were maintained. After the iron chloride was added, a pale olive green precipitate formed. The precipitate was separated from the supernatant via gravity filtration and dried under an argon stream at room temperature for several hours. When the material had acquired sufficient body to hold its shape after extrusion it was place into a 50 ml syringe and extruded into noodle-like shapes. The "noodles" were placed into a shallow glass dish. The shaped material was permitted to further air dry over 12 hours. When dry the material was brittle and olive drab, becoming orange/brown upon several days of exposure to air. The final sample consisted of 2–3 mm×5–15 mm cylinders.

Sample 3

A buffered 6.5 molal lithium malonate solution was prepared by adjusting the pH of a 6.5 m aqueous malonic acid solution to 6.0 using lithium hydroxide powder. An aqueous 6.8 molal aqueous $FeCl_2$ solution was prepared. "Water Glass" was prepared as in Example 1. Using these solutions, 0.136 moles $FeCl_2$ was added in one aliquot to 0.065 moles malonate with vigorous stirring under an inert atmosphere at room temperature. After five minutes, 0.136 moles of $Na_2CO_3$ was added in small amounts over 15 minutes with continued stirring. The solution was stirred for five additional minutes and then left quiescent under an argon blanket for two hours. A dark precipitate settled out during this time. The supernatant liquid was decanted. The precipitate was separated from residual water by gravity filtration and washed with twice its volume of deionized water using two equal aliquots. The dark, rubbery material thus isolated was dried under an argon stream at room temperature for 48 hours. The dried material was mixed with 5.3 times its weight of the "water glass" solution. It became plastic with a granular texture. This material was formed into a sheet $^1\!/_8$–$^3\!/_{16}$" thick on a glass plate. After 1 hour of drying in the air at room temperature, the dough-like sheet was cut into squares approximately ¼" on a side and permitted to air dry at room temperature an additional 48 hours. After 48 hours the sample was hard, dark, and glassy.

Sample 4

Aqueous solutions of 3.1 molal $FeCl_2$, 1.25 molal $NaHCO_3$, and 3.84 molal malic acid were prepared. Using these solutions, 0.304 moles $FeCl_2$ was measured into a flask and placed under a nitrogen sparge. 0.499 moles malic acid was added to the iron chloride solution quickly at room temperature in one aliquot with vigorous stirring while maintaining the nitrogen sparge. With continued stirring and nitrogen purge, 0.501 moles $NaHCO_3$ was added. The resulting solution was stirred gently under a nitrogen blanket at room temperature for 12 hours. After 12 hours the thick, dark liquid was transferred into a bottle fitted with a nitrogen jet. The water remaining in the suspension was evaporated using the jet until the solid material hardened. The resulting light olive green material crumbled easily, and was pulverized by pressing on it with a plastic rod. The fragments were classified in analytical sieves, the fraction passing 20 mesh and retained on 40 mesh being saved.

Sample 5

Aqueous solutions of 1.50 m $NaHCO_3$, 1.00 m $FeCl_2$, 1.51 m LiOH, and 1.75 m malic acid were prepared. A commercially available sodium silicate solution nominally containing 11.0% $Na_2O$ and 31.7% $SiO_2$ and having a density of 1.47 was obtained (Philadelphia Quartz). Using these solutions, 0.150 moles $FeCl_2$ was poured concurrently with 0.300 moles $NaHCO_3$ into a third vessel which was being purged with a stream of nitrogen and vigorously agitated. After the entirety of the two solutions had been combined, an additional 0.150 moles $NaHCO_3$ was poured in one aliquot into the combined solution, with continued stirring and nitrogen purge. The vessel was subjected to gentle heating (30°–40° C. on an electric hot plate) and vigorously stirred under an nitrogen blanket for 0.5 hour.

At the end of the 0.5 hour reaction time, 0.302 moles LiOH was added in one aliquot by pouring it into the reaction mixture under nitrogen purge. The reaction mixture was stirred under a nitrogen blanket at 35°–45° C. for fifteen minutes. 0.175 moles malic acid was added in one aliquot. The reaction mixture was agitated (magnetic stir bar and nitrogen sparge) vigorously for 90 minutes, while the temperature was maintained at 35°–45° C. 0.05 moles soduim silicate was added by pouring 14.087 g of the commercial sodium silicate solution into the reaction mixture. Following this addition the mixture was stirred for a further two hours under nitrogen. Heating and agitation were discontinued, and the precipitate which had formed from the reaction mixture was allowed to settle out under a nitrogen blanket over 48 hours. After 48 hours the precipitate was separated from the supernatant by gravity filtration. The resulting light tan/green to dark olive green gelatinous precipitate was shaped in the form of round "noodles" using a piston extrusion device and permitted to dry in the air for 24 hours. The hard, brittle "noodles" were broken into pieces ¼ inch to ½ inch long with a spatula and placed into a sealed bottle.

Sample 6

Solutions of 1.00 m aqueous $FeCl_2$, 1.50 m succinic acid in 11% ehanol/89% water, 5.30 m aqueous LiOH, and 2.30 m aqueous $Na_2CO_3$ were prepared. A commercial sodium silicate solution nominally containing 11% $Na_2O$ and 31.7% $SiO_2$ and having a density of 1.47 was obtained (Philadelphia Quartz). Using these solutions, 0.10 moles of $FeCl_2$ was placed in a reaction vessel under a nitrogen blanket and agitated with a magnetic stir bar. The solution temperature was maintained 35°–40° C. throughout the synthesis. Into the iron chloride solution 0.05 moles succinic acid was added by pouring the entire amount of the acid solution into the iron chloride solution in one aliquot over a short period of time. Following this addition the tube conducting nitrogen into the reaction vessel was lowered into the reaction mixture to act as a sparging device. 0.05 moles LiOH was added in the same manner as the acid solution. The reaction conditions were maintained following the base addition, and the reaction mixture was agitated for 0.5 hour. After this agitation period 0.15 moles of $Na_2CO_3$ was added to the blue/gray reaction mixture using the same technique as for the two previous additions. The reaction mixture was then vigorously agitated for 1 hour.

At the end of 1 hour the heat source and stirring were removed from the reaction mixture, and the dark precipitate was permitted to settle out over 12 hours. This precipitate was separated from the supernatant by decantation. The resulting muddy material was placed in a bottle and dried further under a nitrogen jet. After several hours of drying the material acquired a gelatinous consistency. This material was then mixed with an amount of the commercial sodium silicate solution nominally containing 0.10 moles of sodium silicate and shaped using a piston extrusion device. The resulting "noodle-like" shapes were placed on a glass sheet and dried to hardness under a nitrogen jet. The dry noodles (3–4 mm diameter by 0.5–1.0 cm long) were dark gray/blue/green, hard, and brittle.

Sample 7

Aqueous solutions of 3.00 m $FeCl_2$, 1.50 m LiOH, and 0.755 m $Na_2CO_3$ were prepared. 100 g deionized, room temperature water was placed in a reaction vessel sparged with argon and agitated with a magnetic stir bar. An argon blanket was kept over the reaction mixture throughout additions. A slurry was made by adding 0.150 moles adipic acid to the deionized water at room temperature. Using the solutions prepared earlier, 0.150 moles LiOH was poured into the slurry in one aliquot with stirring, resulting in a yellow solution. Into this solution was poured 0.300 moles $FeCl_2$ in one aliquot. The addition of the iron chloride produced a brown solution and white precipitate. An additional 150 g of room temperature water was added following addition of the $FeCl_2$.

0.151 moles $Na_2CO_3$ was added to the reaction mixture in one aliquot. Vigorous effervescence accompanied this addition. Following carbonate addition the reaction mixture was heated to 35°–45° C. and stirred for 3 hours under argon. After 3 hours the material was poured into a storage bottle and the brown/white precipitate was allowed to settle out of the dark solution. The precipitate was isolated by vacuum filtration and dried to hardness using a nitrogen jet over the next several weeks.

Sample 8

Aqueous solutions of 2.67 molar (M) $FeCl_2$, 1.2 m $NaHCO_3$, 2.00 m LiOH, and 0.6 m citric acid were prepared. A commercial sodium silicate solution nominally containing 11.0% $Na_2O$ and 31.7% $SiO_2$ and having a density of 1.47 was obtained (Philadelphia Quartz). These solutions were used for the following steps. 0.101 moles $FeCl_2$ was placed into a reaction vessel which had been purged with argon simultaneously with 0.300 moles $NaHCO_3$. The mixture was stirred at 30°–40° C. under argon for 90 minutes, whereupon 0.200 moles of LiOH was added in one aliquot with stirring. The reaction mixture was stirred for a further 20 minutes at 30°–40° C. under argon. 0.06 moles of citric acid was then added, and the mixture was stirred for 70 minutes, maintaining the 30°–40° C. temperature and argon blanket.

Following the stirring period, 0.036 moles of sodium silicate was added to the reaction vessel, while maintaining the 30°–40° C. temperature and argon blanket throughout the addition and subsequent agitation period. The reaction mixture was stirred for 20 minutes after silicate addition, and then temperature control and agitation in the reactor were discontinued. The reaction mixture was left unstirred at room temperature for 48 hours. The resulting gel was formed into noodle-like shapes and dried under a stream of nitrogen. The dark olive-green "noodles" were stored in a closed bottle for later use.

Sample 9

Aqueous solutions of 1.75 m $FeCl_2$, 0.993 m oxalic acid, 1.00 m LiOH, and 1.50 m $Na_2CO_3$ were prepared. Using these solutions, 0.100 moles $FeCl_2$ was placed into a reaction vessel purged with nitrogen which had passed through a purifier to remove oxygen. The solution was stirred vigorously at room temperature. 0.0497 moles oxalic acid was added by pouring it into the reaction vessel in one aliquot under nitrogen. 0.0510 moles LiOH was immediately added to the reaction vessel followed by 100 ml of degassed water. The reaction mixture was stirred under nitrogen for 30 minutes. At the end of this time 0.150 moles $Na_2CO_3$ at 30° C. was added to the reaction vessel using the same methodology as the previous additions. The reaction mixture was stirred under nitrogen for an additional 90 minutes, and then the material was left quiescent under nitrogen for 12 hours.

The resulting yellow/white precipitate was separated by decantation and dried under a nitrogen jet until it had the consistency of dry clay. This light colored material crumbled easily to a powder having a size of about 30–180 mesh.

Sample 10

Aqueous solutions of 1.00 m $FeCl_2$, 1.50 m $NaHCO_3$, 1.51 m LiOH, and 1.75 m malic acid were prepared. Using these solutions, 0.150 moles $FeCl_2$ and 0.450 moles $NaHCO_3$ were combined in small aliquots keeping the ratio of $FeCl_2$ and $NaHCO_3$ constant at a mole ratio of 1:3. As the solutions were mixed, the mixture was drained into a vessel containing 3.3 moles of water heated to 50° C. The resulting mixture was stirred for 15 minutes at 50° C. An inert gas blanket was maintained within this vessel throughout the addition and subsequent steps.

After stirring was completed, an amount of the LiOH solution containing 0.300 moles of LiOH was added in one aliquot to the reaction mixture. The temperature and inert blanket were maintained while the reaction mixture was stirred for 15 minutes. At the end of this time 0.180 moles of malic acid was added in a similar manner with all reaction conditions maintained as before. The reaction mixture was agitated for one hour.

At the end of the agitation period, 0.05 moles sodium silicate was added to the reaction mixture. The agitation, temperature, and inert gas blanket were maintained for two hours, and then the reaction mixture was left quiescent for 12 hours at 50° C. under nitrogen. At the end of this time the precipitate was separated from the reaction solution by vacuum filtration. The resulting gel was then formed into cylindrical shapes and dried under a stream of dry, inert gas. The olive-gray solid was stored in a sealed bottle for later use.

Sample 11

Aqueous solutions of 4.30 m $FeCl_2$ and 1.40 m LiOH were prepared and used in subsequent steps. At room temperature and under an argon blanket, a solution was prepared by mixing 0.0825 moles malic acid and 0.0825 moles $NaSO_3H$ as dry powders and then adding the solid mixture slowly to 25 g of water with stirring. Into this solution 0.0826 moles of LiOH was added in one aliquot. 0.133 moles $FeCl_2$ was immediately added to the reaction mixture in one aliquot, at room temperature and under an inert gas blanket. The reaction mixture was vigorously stirred during the addition.

After the iron chloride addition, 0.0826 moles of $Na_2CO_3$ powder was sprinkled into the reaction mixture with the stirring and inert blanket maintained. The reaction mixture was stirred for 30 minutes under the stated conditions, then sealed in a bottle and left quiescent for 24 hours. At the end of this time the precipitate was isolated by vacuum filtration and transferred into a crimp sealed vessel. It was brought to dryness under a stream of dry nitrogen in the sealed bottle, then broken into chunks of serviceable size (8×20 mesh). The material was blue/green in appearance.

Sample 12

Aqueous solutions of 1.50 m $FeCl_2$, 1.50 m malic acid, 1.50 m LiOH, and 1.50 m $Na_2CO_3$ were prepared. 0.150 moles of the malic acid solution was treated with aliquots of the LiOH solution in a beaker at room temperature under an argon blanket with stirring until the pH reached 4.0. The reaction mixture was then gently heated (30°–35° C.), and while maintaining the inert blanket, 0.300 moles of $FeCl_2$ was added in one aliquot. The reaction mixture was stirred for 30 minutes at 30°–35° C. under argon.

At the end of this time the reaction mixture was treated with aliquots of the $Na_2CO_3$ solution until the pH reached 7.0, at 30°–35° C. under argon. The temperature of the reaction mixture was then raised to boiling, and the reaction mixture volume was reduced by boiling off solvent for the next four hours. At the end of this time 0.30 moles sodium silicate was added to the reaction mixture in one aliquot. Heating was discontinued and the resulting reaction mixture was dried to hardness under an inert gas stream over the next 48 hours. The resulting hard material was broken up mechanically and classified on sieves, the material passing through a 12 mesh sieve and being retained on a 20 mesh sieve being saved. The olive-gray solid was stored in a sealed vessel for later use. It was in the form of a 12×20 mesh powder and had a bulk density of 0.43.

Sample 13

Aqueous solutions of 2.0M $FeCl_2$, 3.72 m malic acid, 4.17 m LiOH, and 1.15 m $NaHCO_3H$ were prepared. The solutions were heated to 40° C. and maintained at this temperature during subsequent steps. Using these solutions, 11.34 moles $FeCl_2$ and 31.16 moles $NaHCO_3$ were mixed in a reaction vessel under an anaerobic nitrogen blanket with stirring. The reaction mixture was agitated for one hour. 20.85 moles LiOH was then added to the reaction vessel in one aliquot with stirring. The reaction mixture was agitated for 20 minutes. 11.91 moles of malic acid was added, and the reaction mixture was agitated for an additional hour. A portion of commercially prepared sodium silicate solution nominally containing 3.78 moles of sodium silicate was added in one aliquot, and the reaction mixture was stirred for 20 minutes. At this point, the nitrogen blanket and heating system were turned off and the material was left quiescent for 20 hours at room temperature.

At the end of this time a gelatinous precipitate was separated from the supernatant liquid by vacuum filtration. This gel was formed into cylindrical shapes and dried to hardness under an air stream. The green solid was placed into a closed bottle for storage.

While the invention has been described herein with reference to specific aspects, features, and embodiments, it will be apparent that other variations, modifications, and embodiments are possible, and all such variations, modifications, and embodiments therefore are to be regarded as being within the spirit and scope of the invention.

What is claimed is:

1. A process for recovery of halocarbon from a gas mixture comprising:
   (i) halocarbon selected from the group consisting of perfluorocarbons, fluorinated hydrocarbons, chlorofluorocarbons, sulfur hexafluoride, and mixtures thereof, and
   (ii) at least one other gas component selected from the group consisting of HF, $WOF_3$, CO, $CO_2$, $F_2O_2$, $F_2$, $Si_2F_6$, $F_2O$, $SiF_4$, $AsH_3$, $BCl_3$, $SiH_4$, $Ta(OC_2H_5)_5$, $Cl_2$, HCl, $N_2$ and $O_2$, wherein the halocarbon is present in a concentration not exceeding 5% by weight, based on the total weight of the gas mixture, said process comprising the steps of:
   a. contacting the gas mixture with a scavenger composition to remove said at least one other gas component from the gas mixture, thereby yielding a first effluent gas mixture containing said halocarbon and substantially free of said at least one other gas component, wherein said scavenger composition is selected from the group consisting of:
      (I) a caustic liquid medium; and
      (II) a solid scavenger material selected from the group consisting of:
         (a) goethite;
         (b) copper oxide;
         (c) copper oxide/zinc oxide mixtures;
         (d) copper sulfate;
         (e) lithium hydroxide;
         (f) a synthetic metallic scavenger comprising a three-dimensional complex of a plurality of (i) metal coordination atoms each of which has coordinated thereto at least two (ii) oxomeric moieties selected from the group consisting of carbonate, sulfite, carboxylate, and silicate, wherein the oxomeric moieties bridge between and link the metal coordination atoms, and each of the metal coordination atoms is bridged to another of the metal coordination atoms through the oxomeric moieties, with the three-dimensional complex comprising at least two different oxomeric moieties of said group; and
      (g) mixtures thereof;
   b. contacting the first effluent gas mixture with an adsorbent which is adsorbingly selective for the halocarbon component of the first effluent gas mixture to adsorb said halocarbon component on the adsorbent and yield a second effluent gas, wherein said contacting with the absorbent is carried out in at least two absorbent beds via pressure swing adsorption processing of the first effluent gas mixture.; and
   c. recovering the adsorbed halocarbon by desorbing same from the adsorbent.

2. A process according to claim 1, wherein the pressure swing adsorption processing comprises provision of two adsorbent beds joined at inlet and outlet ends thereof to gas feed and gas discharge manifolds, respectively, wherein said first effluent gas mixture is introduced to one of said adsorbent beds at superatmospheric pressure to effect adsorption of halocarbon on the bed, and contemporaneously the other adsorbent bed is depressurized following adsorption of halocarbon thereon, to desorb the adsorbed halocarbon and to discharge same from the bed at lower-than-first superatmospheric pressure, and wherein such steps are alternatively and repetitively carried out in the respective adsorbent beds.

3. A process according to claim 2, wherein the discharged halocarbon is compressed and flowed to a gas cylinder.

4. A process for recovery of halocarbon from a gas mixture comprising:
   (i) halocarbon selected from the group consisting of perfluorocarbons, fluorinated hydrocarbons, chlorofluorocarbons, sulfur hexafluoride, and mixtures thereof, and
   (ii) at least one other gas component selected from the group consisting of HF, $WOF_3$, CO, $CO_2$, $F_2O_2$, $F_2$, $Si_2F_6$, $F_2O$, $SiF_4$, $AsH_3$, $BCl_3$, $SiH_4$, $Ta(OC_2H_5)_5$, $Cl_2$, HCl, $N_2$ and $O_2$, wherein the halocarbon is present in a concentration not exceeding 5% by weight, based on the total weight of the gas mixture, said process comprising the steps of:
   a. contacting the gas mixture with a scavenger composition to remove said at least one other gas component from the gas mixture, thereby yielding a first effluent gas mixture containing said halocarbon and substantially free of said at least one other gas component, wherein said scavenger composition is selected from the group consisting of:
      (I) a caustic liquid medium; and
      (II) a solid scavenger material selected from the group consisting of:
         (a) goethite;
         (b) copper oxide;
         (c) copper oxide/zinc oxide mixtures;
         (d) copper sulfate;
         (e) lithium hydroxide;
         (f) a synthetic metallic scavenger comprising a three-dimensional complex of a plurality of (i) metal coordination atoms each of which has coordinated thereto at least two (ii) oxomeric moieties selected from the group consisting of carbonate, sulfite, carboxylate, and silicate, wherein the oxomeric moieties bridge between and link the metal coordination atoms, and each of the metal coordination atoms is bridged to another of the metal coordination atoms through the oxomeric moieties, with the three-dimensional complex comprising at least two different oxomeric moieties of said group; and (g) mixtures thereof;

b. contacting the first effluent gas mixture with an adsorbent which is adsorbingly selective for the halocarbon component of the first effluent gas mixture to adsorb said halocarbon component on the adsorbent and yield a second effluent gas, wherein said first effluent gas mixture contacted with said adsorbent is confined against a selective membrane allowing passage therethrough of non-halocarbon component(s), to concentrate the halocarbon components and allow discharge from the process of gas components other than halocarbon components; and c. recovering the adsorbed halocarbon by desorbing same from the adsorbent.

5. A process for recovery of halocarbon from a gas mixture comprising:

(i) halocarbon selected from the group consisting of perfluorocarbons, fluorinated hydrocarbons, chlorofluorocarbons, sulfur hexafluoride, and mixtures thereof, and (ii) at least one other gas component selected from the group consisting of $HF$, $WOF_3$, $CO$, $CO_2$, $F_2O_2$, $F_2$, $Si_2F_6$, $F_2O$, $SiF_4$, $AsH_3$, $BCl_3$, $SiH_4$, $Ta(OC_2H_5)_5$, $Cl_2$, $HCl$, $N_2$ and $O_2$, wherein the halocarbon is present in a concentration not exceeding 5% by weight, based on the total weight of the gas mixture, said process comprising the steps of:

a. contacting the gas mixture with a scavenger composition to remove said at least one other gas component from the gas mixture, thereby yielding a first effluent gas mixture containing said halocarbon and substantially free of said at least one other gas component, wherein the scavenger composition comprises a caustic liquid medium;

b. contacting the first effluent gas mixture with an adsorbent which is adsorbingly selective for the halocarbon component of the first effluent gas mixture to adsorb said halocarbon component on the adsorbent and yield a second effluent gas; and c. recovering the adsorbed halocarbon by desorbing same from the adsorbent.

6. A process for recovery of halocarbon from a process effluent gas stream containing (a) said halocarbon, selected from the group consisting of perfluorocarbons, fluorinated hydrocarbons, chlorofluorocarbons, sulfur hexafluoride, and mixtures thereof, and (b) acid gas component(s), said process comprising the steps of:

contacting the process effluent gas stream containing said halocarbon with a scavenger composition to remove said acid gas component(s) from the process effluent gas stream, thereby yielding a first effluent gas mixture containing said halocarbon;

contacting the first effluent gas mixture with an adsorbent for the halocarbon component of the first effluent gas mixture, to adsorb said halocarbon component on the adsorbent; and recovering the adsorbed halocarbon by desorbing same from the adsorbent, wherein the steps of contacting the first effluent gas mixture with an adsorbent for the halocarbon component of the first effluent gas mixture, to adsorb said halocarbon component on the adsorbent, and recovering the adsorbed halocarbon by desorbing same from the adsorbent, comprise pressure swing adsorption/desorption.

7. A process for recovery of halocarbon from a gas mixture comprising (i) halocarbon selected from the group consisting of perfluorocarbons, fluorinated hydrocarbons, chlorofluorocarbons, sulfur hexafluoride, and mixtures thereof, and (ii) at least one other gas component, said process comprising the steps of:

contacting the gas mixture with a scavenger composition to remove said at least one other gas component from the gas mixture, thereby yielding a first effluent gas mixture containing said halocarbon and substantially free of said at least one other gas component;

contacting the first effluent gas mixture with an adsorbent which is adsorbingly selective for the halocarbon component of the first effluent gas mixture to adsorb said halocarbon component on the adsorbent and yield a second effluent gas, and recovering the adsorbed halocarbon by desorbing same from the adsorbent, wherein said adsorbent contacting is carried out in at least two adsorbent beds via pressure swing adsorption processing of the first effluent gas mixture.

8. A process for recovery of halocarbon from a gas mixture comprising (i) halocarbon selected from the group consisting of perfluorocarbons, fluorinated hydrocarbons, chlorofluorocarbons, sulfur hexafluoride, and mixtures thereof, and (ii) at least one other gas component, said process comprising the steps of:

contacting the gas mixture with a scavenger composition to remove said at least one other gas component from the gas mixture, thereby yielding a first effluent gas mixture containing said halocarbon and substantially free of said at least one other gas component;

contacting the first effluent gas mixture with an adsorbent which is adsorbingly selective for the halocarbon component of the first effluent gas mixture to adsorb said halocarbon component on the adsorbent and yield a second effluent gas, and recovering the adsorbed halocarbon by desorbing same from the adsorbent, wherein first effluent gas mixture contacted with said adsorbent is confined against a selective membrane allowing passage therethrough of non-halocarbon component(s), to concentrate the halocarbon components and allow discharge from the process of gas components other than halocarbon components.

9. A process for recovery of halocarbon from a gas mixture comprising (i) halocarbon selected from the group consisting of perfluorocarbons, fluorinated hydrocarbons, chlorofluorocarbons, sulfur hexafluoride, and mixtures thereof, and (ii) at least one other gas component, said process comprising the steps of:

contacting the gas mixture with a caustic liquid medium to remove said at least one other gas component from the gas mixture, thereby yielding a first effluent gas mixture containing said halocarbon and substantially free of said at least one other gas component;

contacting the first effluent gas mixture with an adsorbent which is adsorbingly selective for the halocarbon component of the first effluent gas mixture to adsorb said halocarbon component on the adsorbent and yield a second effluent gas, and recovering the adsorbed halocarbon by desorbing same from the adsorbent.

* * * * *